(12) United States Patent
Lim et al.

(10) Patent No.: US 8,815,572 B2
(45) Date of Patent: Aug. 26, 2014

(54) NUCLEIC ACID EXTRACTION APPARATUS

(75) Inventors: Geun-Bae Lim, Pohang-si (KR); Ji-Min Kahng, Seoul (KR); Jin-Hwa Jung, Pohang-si (KR); Ho-Taik Kwon, Seoul (KR)

(73) Assignee: Postech Academy-Industry Foundation, Pohang (KR)

( * ) Notice: Subject to any disclaimer, the term of this patent is extended or adjusted under 35 U.S.C. 154(b) by 240 days.

(21) Appl. No.: 13/001,441

(22) PCT Filed: Jun. 22, 2009

(86) PCT No.: PCT/KR2009/003340
§ 371 (c)(1),
(2), (4) Date: Aug. 17, 2011

(87) PCT Pub. No.: WO2009/157679
PCT Pub. Date: Dec. 30, 2009

(65) Prior Publication Data
US 2011/0300609 A1    Dec. 8, 2011

(30) Foreign Application Priority Data
Jun. 27, 2008    (KR) .......................... 10-2008-0061902

(51) Int. Cl.
*C12M 1/00*    (2006.01)
*B01J 19/00*    (2006.01)
*B01L 3/00*    (2006.01)
*C12N 15/10*    (2006.01)

(52) U.S. Cl.
CPC .............. *C12N 15/1003* (2013.01); *B01L 3/502* (2013.01); *B01L 2200/0631* (2013.01); *B01L 2300/069* (2013.01); *B01L 2300/0832* (2013.01); *B01L 2300/0681* (2013.01)

USPC ................... 435/283.1; 435/267.1; 435/287.3; 435/288.5; 435/288.7

(58) Field of Classification Search
CPC .................. B01L 2200/0631; B01L 2300/068; B01L 2300/069; B01L 2300/0832; B01L 3/502; B01L 3/5021; C12N 15/1003
USPC .......... 435/283.1, 287.1–287.3, 288.5–288.7, 435/6.1, 34
See application file for complete search history.

(56) References Cited

U.S. PATENT DOCUMENTS

| 4,750,982 A | 6/1988 | Tomblin et al. |
| 6,277,648 B1 | 8/2001 | Colpan |

(Continued)

FOREIGN PATENT DOCUMENTS

| CN | 1299413 | 6/2001 |
| JP | 2001-321200 A | 11/2001 |
| KR | 10-1999-0082777 | 1/2001 |

OTHER PUBLICATIONS

Voytas, "Current Protocols in Molecular Biology", Chapter II, section II, John Wiley & Sons, 2000, pp. 2.5 A.1-2.5 A.9.*

(Continued)

*Primary Examiner* — Michael Marcheschi
*Assistant Examiner* — Shanta G Doe
(74) *Attorney, Agent, or Firm* — Lexyoume IP Meister, PLLC (57) ABSTRACT

The present invention relates to a nucleic acid extracting apparatus, and the nucleic acid extracting apparatus can include a pipe-shaped tube having an open outlet at one side thereof, and a hydrogel supporting member that is provided inside the tube and filters impurities excluding an extraction target material.

6 Claims, 6 Drawing Sheets

(56) References Cited

U.S. PATENT DOCUMENTS

| | | |
|---|---|---|
| 2001/0047966 A1 | 12/2001 | Colpan |
| 2002/0012982 A1* | 1/2002 | Blakesley et al. ............ 435/183 |
| 2002/0192656 A1* | 12/2002 | Richardson et al. ............ 435/6 |
| 2004/0072375 A1 | 4/2004 | Gjerde et al. |

OTHER PUBLICATIONS

Watanabe M. "Rapid and inexpensive recovery method of DNA fragments from agarose and polyacrylamide gels by a cotton-wool column tube", Nucleic Acids Symposium Series, 1999, No. 42, pp. 101-102.

Wang Z, Rossman TG. "Isolation of DNA fragments from agarose gel by centrifugation", Nucleic Acids Research, 1994, vol. 22, No. 14, pp. 2862-2863.

Gubin AN, Kincaid RL. "A pressure-extrusion method for DNA extraction from agarose gels", Analytical Biochemistry, vol. 258, Iss. 1, Apr. 10, 1998, pp. 150-152.

Daniel N. Miller, "Evaluation of gel filtration resins for the removal of PCR-inhibitory substances from soils and sediments", Journal of Microbiological Methods, vol. 44, No. 1, Feb. 1, 2001, pp. 49-58.

State Intellectual Property Office of the People's Republic of China, Search Report dated Jan. 25, 2013, which was attached to the Office Action dated Jan. 31, 2013, of the corresponding Chinese Patent Application No. 200980134053.X.

Daniel Voytas, "Resolution and Recovery of large DNA fragments", Current Protocols in Molecular Biology, Chapter II, section II, p. 2.5 A.3-2.5 A.4, Juhn Wiley & Sons, Inc. (May 1, 2001).

Chinese Patent Office, Search Report dated Dec. 24, 2013, which was attached to the Office Action dated Jan. 6, 2014 of the corresponding Chinese Patent Application No. 200980134053.X.

\* cited by examiner

NUCLEIC ACID EXTRACTION APPARATUS

TECHNICAL FIELD

The present invention relates to a nucleic acid extracting apparatus, and more particularly, it relates to a nucleic acid extracting apparatus that uses a hydrogel column as a supporting member.

BACKGROUND ART

Recently, as causes of diseases has been explained at the gene level based on results of human genome studies, demand for modification and biochemical analysis of biological specimens for the purpose of cure and prevention of diseases has increased. In addition, a technique for extracting and analyzing nucleic acid from biological specimens or cell-included specimens is demanded not only for diagnosis of disease but also in various fields such as new drug discovery and development, pretesting for viral or bacteria infection, and forensic medicine.

When nucleic acid is extracted, low-purity nucleic acid suppresses or disturbs a hybridization reaction such as with Southern blotting and a chemical reaction such as an enzyme reaction, and nucleic acid contaminating material dissolves nucleic acid to be tested and causes an error in measurement of nucleic acid quantity. Such a contaminating material includes a low-molecular material such as fat, an enzyme inhibitor, an enzyme such as a protein, a polysaccharide, and a polynucleotide.

In order to maintain a high-purity nucleic acid for application to molecular biology, various methods have been developed for solving the above-stated problems.

A method for extracting nucleic acid from a cell includes a method in which a specimen including the cell is solubilized by being processed with sodium dodecyl sulfate (SDS) or proteinase K and then protein is denaturalized and eliminated with penyol so as to refine the nucleic acid. However, the phenol extraction method takes a long time since it includes many steps, and nucleic acid extraction efficiency greatly depends on skill of a worker.

Therefore, recently, a kit using a column has become a basic tool for nucleic acid extraction in order to reduce the above-stated problems. This tool uses a method with silica or fiberglass that uniquely combines with nucleic acid, and the method dissolves a cell by processing it with a chaotropic reagent and refines nucleic acid molecules from protein and other materials in the cell by using a structural interactive mechanism between a water molecule and nucleic acid.

The fiberglass or silica film has a low-combination ratio with a cell metabolic material, and therefore relatively highly-concentrated nucleic acid can be obtained. Although this method is more simple compared to the phenol extraction method, this method has drawbacks in complexity of operation and time consumption because the chaotropic reagent or ethanol that strongly blocks an enzyme reaction such as PCR should be completely eliminated.

Recently, a method for directly refining nucleic acid by using a filter has been disclosed in the Internal Publication No. WO 00/21973. In this method, a cell is attached to a filter by passing a specimen through the filter, the attached cell is dissolved and filtered through the filter, and then nucleic acid attached to the filter is washed and eluted. However, in order to elute nucleic acid after attaching the cell to the filter, the filter should be selected in accordance with a cell type.

The above information disclosed in this Background section is only for enhancement of understanding of the background of the invention and therefore it may contain information that does not form the prior art that is already known in this country to a person of ordinary skill in the art.

DETAILED DESCRIPTION

Technical Problem

To solve the above problems, the present invention has been made in an effort to provide an extracting apparatus that can more stably and easily extract nucleic acid.

Technical Solution

A nucleic acid extracting apparatus according to an exemplary embodiment of the present invention may include a pipe-shaped tube having an open outlet at one end thereof, and a hydrogel supporting member that is provided inside the tube and filters impurities excluding an extraction target material.

The nucleic acid extracting apparatus may further include a housing in which the tube is inserted and connected with the outlet, and having one side formed in a closed pipe shape. The hydrogel supporting member may be formed of an agarose gel, and the agarose gel may include 1% to 2% agarose. Further, the agarose gel may include 0.5% to 5% agarose.

An injection groove extending in the length direction of the tube may be formed on an upper surface of the hydrogel supporting member, and the injection groove may be formed in a center portion of the hydrogel supporting member. In addition, a plurality of pressure reducing holes that contact the hydrogel supporting member may be formed at an external circumference of the tube. The hydrogel supporting member may be adhered to an inner surface of the tube, and the hydrogel supporting member may be formed in a rotating body shape.

The nucleic acid extracting apparatus extracts nucleic acid from a cell, and the cell may be a biological sample that may be one selected from a group of an animal sample, a plant sample, or a microscopic organism sample, or may be a human-derived cell that includes blood, blood serum, blood plasma, bone marrow, urine, feces, sputum, cell aspirate, tissue, and a tissue-derived material.

The nucleic acid extracting apparatus may be provided in a centrifugal separator, and the nucleic acid may be DNA. In addition, the nucleic acid extracting apparatus may be applied to nucleic acid extraction in a DNA chip test, and may be applied to nucleic acid extraction in point-of-care testing.

Advantageous Effects

According to the exemplary embodiment of the present invention, nucleic acid can be easily extracted without impurities by using a hydrogel supporting member as a filter.

In addition, pure nucleic acid can be obtained by using agarose gel as the hydrogel supporting member.

Nucleic acid recovery efficiency can be improved by forming an injection groove in the hydrogel supporting member.

Further, nucleic acid can be more easily extracted while reducing damage to the nucleic acid by forming a pressure-reducing hole in a tube.

<Description of Reference Numerals Indicating Primary Elements in the Drawings>

| | |
|---|---|
| 12: housing | 13: cover |
| 14: tube | 15: pressure reducing hole |
| 16: hydrogel supporting member | 18: injection groove |
| 24: outlet | |

BEST MODE

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

Figure 1:
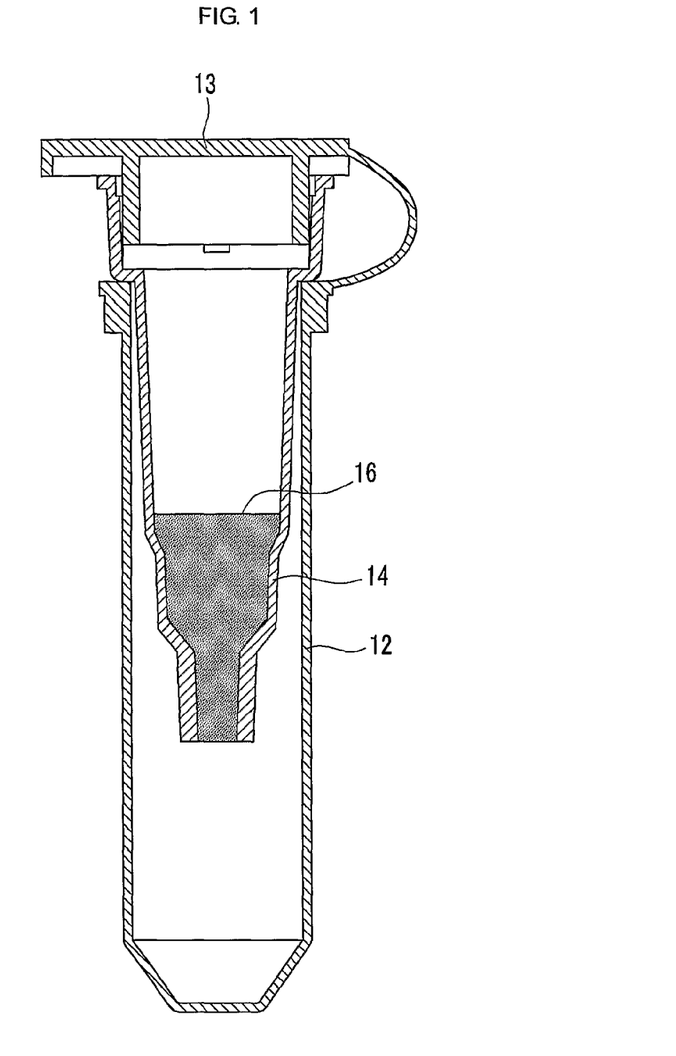
FIG. 1 is a cross-sectional view of a nucleic acid extracting apparatus according to a first exemplary embodiment of the present invention.

FIG. 1 is a cross-sectional view of a nucleic acid extracting apparatus according to a first exemplary embodiment of the present invention.

Referring to FIG. 1, a nucleic acid extracting apparatus according to an exemplary embodiment of the present invention includes a housing 12 that forms an external shape of the nucleic acid extracting apparatus, a tube 14 that is inserted into the housing 12, a hydrogel supporting member 16 installed inside the tube 14, and a cover 13 that covers the tube 14.

The housing 12 is formed of a cylindrical pipe having a space therein, and a lower portion thereof is closed. In addition, the interior diameter of the housing 12 is gradually decreased toward the bottom thereof so that extracted nucleic acid or acid can be collected therein.

The tube 14 is inserted inside the housing, and a space is formed therein for containing a cell extract. An outlet 24 that is open bottomward is formed in a lower portion of the tube 14 so that nucleic acid can move to the housing therethrough. The interior diameter of the outlet 24 is smaller than other portions thereof for passing only nucleic acid excluding proteins and the like therethrough.

The hydrogel supporting member 16 is provided in the tube 14, and has a shape that corresponds to the internal shape of the tube 14. Here, the shape is approximately columnar, has a rotating body.

The hydrogel supporting member 16 in the present exemplary embodiment is formed of agarose gel that can be easily formed and is harmless to the human body. However, the present exemplary embodiment is not limited thereof, and various hydrogels can be applied.

The hydrogel supporting member 16 includes agarose in a concentration of 1.0% to 2.0%, and the volume thereof may be 300 µl to 600 µl.

In application of a centrifugal separating method, when the concentration of the agarose is lower than 1.0% in the hydrogel column 16, the hydrogel column 16 can be easily broken during the centrifugal separation process, and when the concentration of the agarose is higher than 2.0%, an aperture becomes too small to sufficiently extract the nucleic acid.

When pressure or an electrical method is used, the hydrogel column 16 can include agarose at 0.5% to 5.0%. When extracting nucleic acid by using pressure, it is desirable that the hydrogel column 16 includes the agarose at less than 5.0% in order to prevent the hydrogel column 16 from being easily broken. When the agarose is included at more than 5.0%, the pore size thereof is reduced so that the nucleic acid cannot pass through the hydrogel column 16.

In addition, when the electrical method is used, it is advantageous when the size of the pores is relatively large, and therefore it is desirable to include 0.5% or more agarose. When the hydrogel column 16 includes less than 0.5% agarose, the size of the pores becomes too large, and the hydrogel column 16 may by broken due to pressure or a foreign material may be separated through the agarose gel column.

The hydrogel is a polymer material that can contains moisture, and has a three-dimensional network structure in which molecules are connected to each other by chemical and physical combinations. In addition, the hydrogel contains moisture by a hydrophilic functional group, capillary action, and osmotic pressure. Accordingly, the hydrogel has superior air permeability and percolate absorption, and is friendly to blood, body fluids, and body tissue.

The hydrogel supporting member 16 is hydrophilic and has the three-dimensional network structure, and therefore it can function as a nucleic acid filter during the centrifugal separation process. That is, since the nucleic acid included in the cell extract is small in size and is hydrophilic, it may pass through the pores formed in the hydrogel supporting member 16 and be emitted through the outlet 24. However, a relatively large and non-aqueous phase liquid impurity such as a protein cannot pass through the hydrogel supporting member 16 so that it remains in the tube 14.

A process for extracting nucleic acid by using the nucleic acid extracting apparatus according to the present exemplary embodiment will now be described in further detail.

First, a cell extract is obtained. Here, the cell extract refers to a mixture that includes cell components obtained by destroying the cell.

The cell may be formed of a biological sample of an animal, a plant, or a microscopic organism. In addition, the cell may be a human-derived cell that includes blood, blood serum, blood plasma, bone marrow, urine, feces, sputum, cell aspirate, tissue, and a tissue-derived material.

The cell extract can be made by adding a lysis buffer into a container in which a cell is contained, and the lysis buffer may be formed of various commercially available materials. In addition, a proteinase K which is a protein hydrolase or an RNase which is a ribo DNAase may be further included in addition to the lysis buffer.

Next, the hydrogel supporting member 16 is formed in the tube 14. In this case, the hydrogel supporting member 16 is formed of an agarose gel including 2% agarose. However, the concentration of the agarose may be variously changed in accordance with viscosity or concentration of the sample.

After adding the agarose to distilled water, the agarose is dissolved by heating the mixture. Then, the agarose aqueous solution is added into the tube 14 and then the tube 14 is left at room temperature so as to form the column-shaped hydrogel supporting member 16.

The cell extract is inserted into the tube 14 where the hydrogel supporting member 16 is formed and then a centrifugal separating process is performed. In this case, the centrifugal separating process is performed three times, each time taking 5 minutes, at 2000 rpm in a micro-centrifugal separator.

During the centrifugal separating process, DNA passes through the hydrogel supporting member 16 and is emitted to the housing 12 through the outlet 24, and foreign materials such as proteins that cannot pass through the hydrogel remain behind.

In the present exemplary embodiment, the nucleic acid is extracted by using the centrifugal separator, but the present invention is not limited thereto. Therefore, the nucleic acid can be extracted by using pressure or an electrical method, and in this case, the hydrogel supporting member 16 is used as a filter.

The extracted nucleic acid may be used in a genome test or a DNA chip test. That is, the nucleic acid extracting apparatus according to the present exemplary embodiment can be applied to nucleic acid extraction in a genome test or a DNA chip test.

In addition, the nucleic acid extracting apparatus according to the present exemplary embodiment may be applied in nucleic acid extraction in a point-of-care test (generally referred to as POC test). The POC test is a test that can be performed to diagnose a disease of a patient at a clinic or hospital setting or at the home of a patient. The nucleic acid extracting apparatus according to the present exemplary embodiment can be portably used since it can extract nucleic acid with a simple structure, and therefore nucleic acid extracted by the portably extracting apparatus can be easily applied to the POC test.

Figure 2:
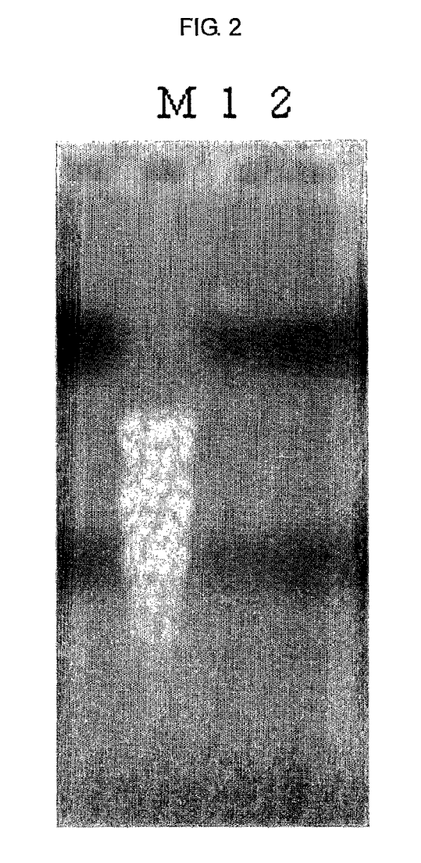
FIG. 2 is an electrophoresis photo of a genomic DNA of MC3T3 osteoblast separated by using the nucleic acid extracting apparatus according to the present invention.

FIG. 2 shows an electrophoresis result of DNA collected by using the housing 12.

FIG. 2 is an electrophoresis photo of genomic DNA of an MC3T3 osteoblast separated by using the nucleic acid extracting apparatus according to the present invention. In FIG. 2, lane M is a standard DNA marker, and lane 1 and lane 2 are electrophoresis results of the genomic DNA of the MC 3T3 osteoblast obtained by using a method according to the present invention.

Figure 3:
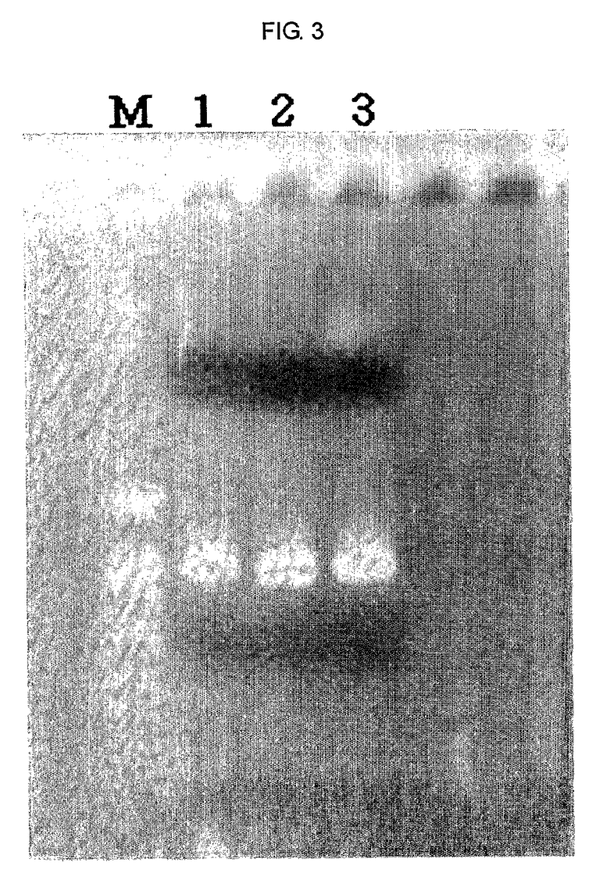
FIG. 3 is a photo of a polymerase chain reaction result for checking purity of the genomic DNA of the MC3T3 osteoblast separated by using the nucleic acid extracting apparatus according to the present invention.

FIG. 3 is a photo of a polymerase chain reaction result for checking purity of the genomic DNA of the MC3T3 osteoblast separated by using the nucleic acid extracting apparatus according to the present invention In FIG. 3, lane M is a standard DNA marker, and lane 1 is an electrophoresis result after amplifying glyceraldehyde-3-phosphate dehydrogenase (G3PHD) in the genomic DNA of the MC3T3 osteoblast obtained by using the method according to the present invention. Lanes 2 and 3 are electrophoresis results after amplifying G3PHD in genomic DNA of the MC3T3 osteoblast obtained by using a commercially available genomic DNA extracting apparatus.

In the present exemplary embodiment, DNA is applied as the nucleic acid, but the present invention is not limited thereto. That is, the present exemplary embodiment can be applied to nucleic acid separation of various kinds, such as RNA.

An experiment for measuring a DNA extraction possibility and a proper gel concentration level from clinical specimens by using an agarose gel supporting member was performed.

In order to exclude an influence of a PCR reaction inhibitor, a test that included a hybridization process was selected from among tests using DNA.

One among cervical swab specimens on which a human papilloma virus (HPV) DNA chip test was selected and DNA extraction was performed on the selected specimen by using a nucleic acid extracting apparatus with an agarose gel supporting member, and an HPV DNA chip test was performed on a result of the DNA extraction. In order to estimate sensitivity, an electrophoresis reading was performed after a general PCR test. The specimen was HPV-58, and Proteinase K at 20 µl, a specimen for HPV test at 400 µl, and a lysis buffer at 200 µl were added into a tube where the agarose gel supporting member was present, and then centrifugal separation was performed three times for 5 minutes each time at 2000 RPM/200 RCF. As the agarose supporting member, a supporting member having a volume of 0.3 ml and a supporting member having a volume of 0.6 ml were used.

When reading a result of the general PCR test with electrophoresis, results of both the 0.3 ml and 0.6 ml at columns could be read only at a 2% agarose gel concentration. Meanwhile, in the DNA chip test in which a result can be obtained even if the number of DNA copies is low, an accurate HPV type result could be obtained in an agarose gel concentration of 1%, 1.5%, and 2% in the 0.3 ml supporting member and in an agarose gel concentration of 2% in the 0.6 ml supporting member.

According to the results of the present experiment, the general PCR test and the DNA chip test for obtaining HPV type information could be performed on both the 0.3 ml and 0.6 ml supporting members when agarose gel of 2% was used.

The following Table 1 shows experiment conditions of each lane.

|  | 0.3 ml | | | 0.6 ml | | |
|---|---|---|---|---|---|---|
|  | Specimen No. | | | | | |
|  | 1 | 2 | 3 | 4 | 5 | 6 |
| Agarose concentration | 1.0% | 1.5% | 2.0% | 1.0% | 1.5% | 2.0% |
| Agarose pore size | 150 nm | 500 nm | | 150 nm | 500 nm | |
| Electrophoresis result | − | − | + | − | − | + |
| HPV DNA Chip | Pos 58 | Pos 58 | Pos 58 | Fail | Fail | Pos 58 |

Figure 4:
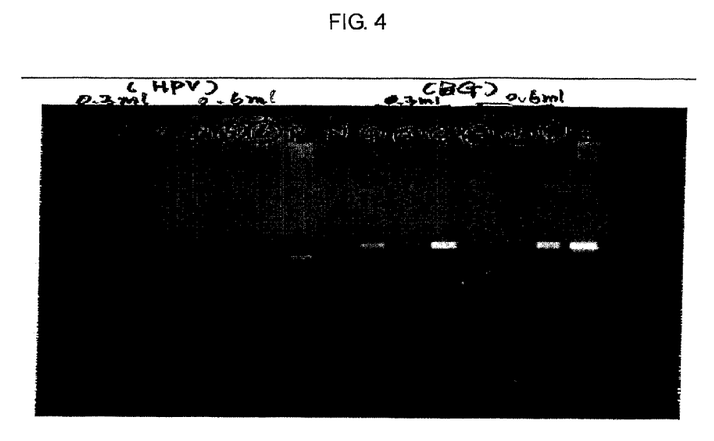
FIG. 4 is a photo of an electrophoresis result after PCR of nucleic acid of an HPV cell extracted by using the nucleic acid extracting apparatus according to the first exemplary embodiment of the present invention.
Figure 5:
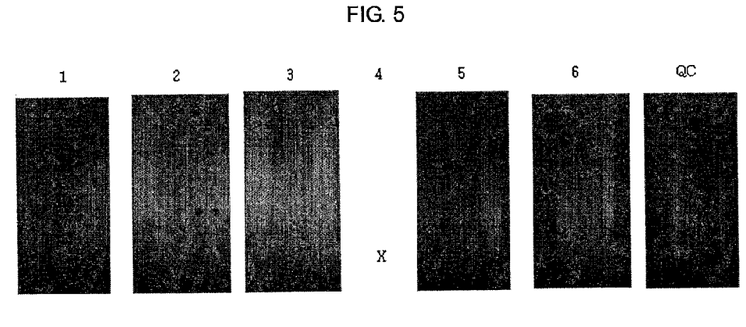
FIG. 5 is a photo of a nucleic acid chip test result of nucleic acid of the HPV cell extracted by using the nucleic acid extracting apparatus according to the first exemplary embodiment of the present invention.

FIG. 4 is a photo showing an electrophoresis result after a PCR test was performed, and FIG. 5 is a photo of a DNA chip test result.

As shown in FIG. 4 and FIG. 5, when a result of a general PCR test is read with electrophoresis, the result could be read only when both of the 0.3 ml and 0.6 ml columns are in an agarose gel of 2%. Meanwhile, in the DNA chip test in which a result can be obtained even though the number of DNA copies is low, an accurate HPV type result could be obtained in agarose gel of 1%, 1.5%, and 2% in the 0.3 ml supporting member and in agarose gel of 2% in the 0.6 ml supporting member.

According to the results of the experiment, the general PCR test and the DNA chip test for obtaining HPV type information could be performed on both the 0.3 ml and 0.6 ml supporting members when agarose gel of 2% was used.

An experiment was performed to compare the nucleic acid extracting apparatus according to the present exemplary embodiment with a nucleic acid extracting method that has been commonly used so as to evaluate the nucleic acid extraction efficiency of the nucleic acid extracting apparatus of the present exemplary embodiment.

For nucleic acid extraction of a clinical specimen stored in the nucleic acid extracted state, nucleic acid was extracted by using a commonly used nucleic acid extracting apparatus and the nucleic acid extracting apparatus according to the present exemplary embodiment, and then a recovery ratios of each method were compared by measuring concentrations of the extracted nucleic acid.

HPV-18 was used as a specimen, and proteinase K at 20 μl, DNA extraction specimen at 200 μl, and lysis buffer at 200 μl were added to the specimen, and centrifugal separation was performed on the mixture at 2000 RPM/200 RCF for 15 minutes. In the experiment, the agarose gel at a concentration of 2.0% and the hydrogel supporting members respectively having 0.3 ml and 0.6 ml volumes were used. With reference to DNA-acid concentration of 65 μg/ml of DNA extract used in the test, the commonly-used nucleic acid extracting method provides 14 μg/ml, that is, approximately a 21.5% recovery rate, and 2% agarose gel 0.3 ml and 0.6 ml respectively provided 19 μg/ml and 10 μg/ml, that is, approximately 29.2% and 15.4% recovery rates. Therefore, the result of the comparison demonstrates that the efficiency of the nucleic acid extracting apparatus of the present exemplary embodiment is included within a range for clinical application. As described, the nucleic acid extracting apparatus of the present exemplary embodiment is particularly advantageous to extract DNA of a biological specimen.

Figure 6:
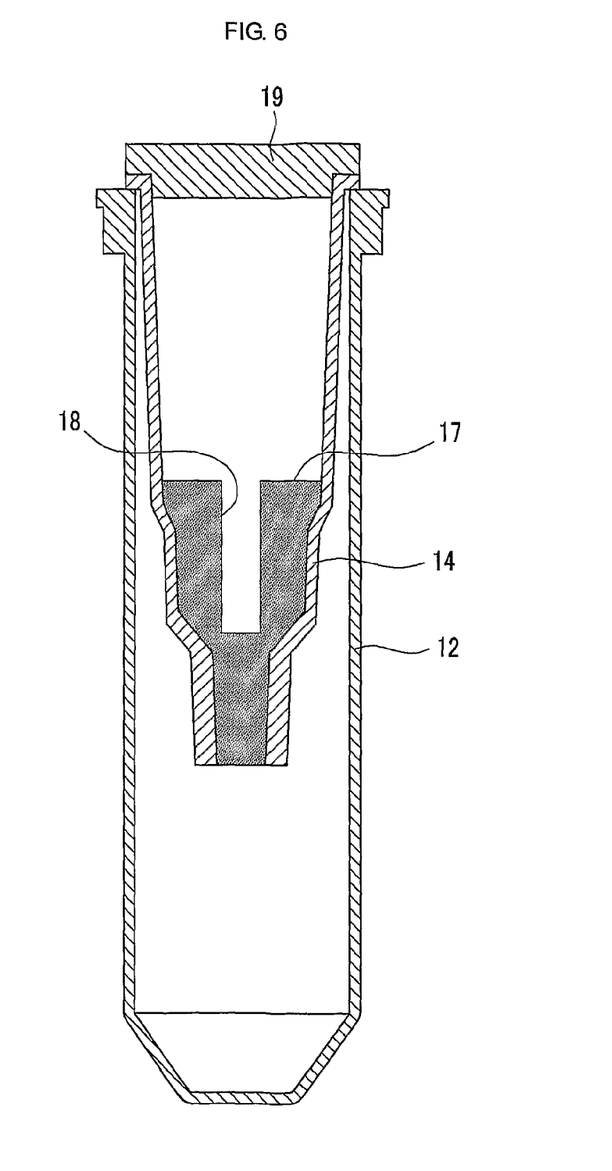
FIG. 6 is a cross-sectional view of a nucleic acid extracting apparatus according to a second exemplary embodiment of the present invention.

FIG. 6 is a cross-sectional view of a nucleic acid extracting apparatus according to a second exemplary embodiment of the present invention.

Referring to FIG. 6, a nucleic acid extracting apparatus according to the present exemplary embodiment includes a cylindrical housing 12, a tube 14 inserted inside the housing 12, a hydrogel supporting member 17 provided in the tube 14, and a cover 19 that covers the tube 14.

An injection groove 18 is formed inside the hydrogel supporting member 17 according to the present exemplary embodiment. The injection groove 18 is formed in a center portion of the hydrogel supporting member 17, and may be formed in a cylindrical shape. Such an injection groove 18 can contain cell extract, and reduces a distance between an outlet 24 and the cell extract, thereby improving nucleic acid recovery efficiency. A plurality of micropores are formed in the hydrogel supporting member 17, and nucleic acid is emitted to the outlet 24 through the plurality of micropores during the centrifugal separation process. Accordingly, when the distance between the cell extract and the outlet 24 is decreased, the nucleic acid can more easily pass through the hydrogel supporting member 17 so that the nucleic acid recovery efficiency can be improved.

Figure 7:
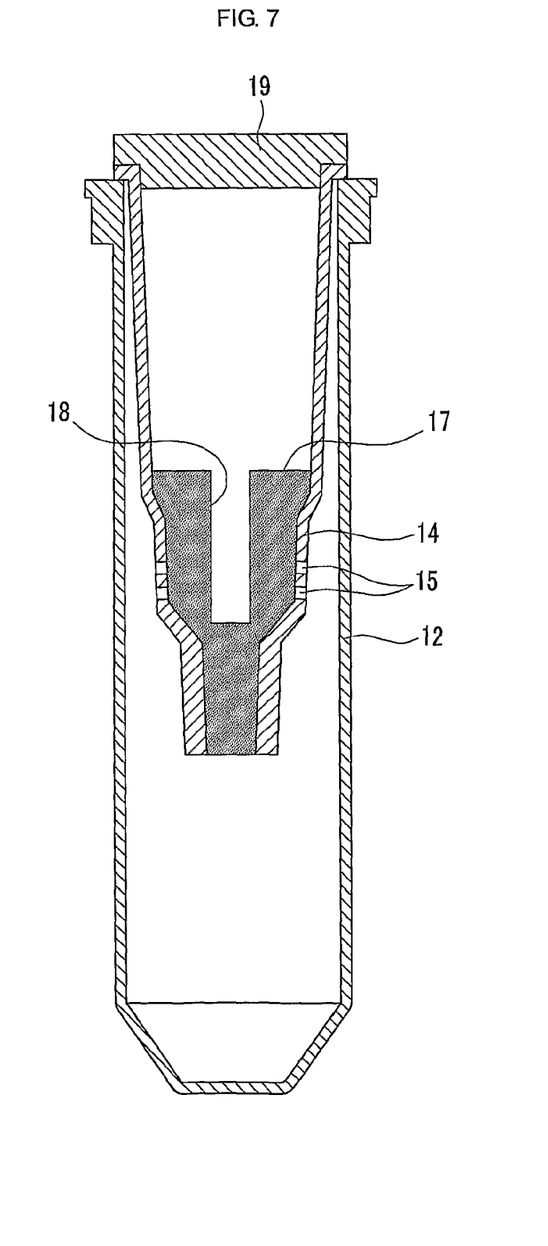
FIG. 7 is a cross-sectional view of a nucleic acid extracting apparatus according to a third exemplary embodiment of the present invention.

FIG. 7 is a cross-sectional view of a nucleic acid extracting apparatus according to a third exemplary embodiment of the present invention.

Referring to FIG. 7, a nucleic acid extracting apparatus according to the present exemplary embodiment includes a cylindrical housing 12, a tube 14 inserted into the housing 12, a hydrogel supporting member 17 installed inside the tube 14, and a cover 19 that covers the tube 14.

A plurality of pressure reducing holes 15 are formed at an external circumference of the tube 14 where the hydrogel supporting member 17 is disposed, and the pressure holes 15 reduce pressure generated due to the centrifugal force. In addition, an injection groove 18 is formed in the hydrogel supporting member 17, and the pressure reducing holes 15 are formed at a side of the injection groove 18. Accordingly, nucleic acid in the injection groove 18 can be emitted to the housing 12 through the pressure reducing grooves 15 so that the nucleic acid recovery efficiency can be further improved.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A nucleic acid extracting apparatus comprising:
   a pipe-shaped tube having an open outlet at one end thereof; and
   a hydrogel member provided inside the tube and filtering impurities excluding an extraction target material,
   wherein an injection groove extending in the length direction of the tube is formed on an upper surface of the hydrogel member and a plurality of pressure reducing holes that contact the hydrogel member are formed at an external circumference of the tube,
   and wherein the pressure reducing holes are formed at a side of the injection groove,
   and the injection groove is formed in a center portion of the hydrogel member, and is formed in a cylindrical shape.

2. The nucleic acid extracting apparatus of claim 1, further comprising a housing in which the tube is inserted and connected with the outlet, and having one side formed in a closed pipe shape.

3. The nucleic acid extracting apparatus of claim 1, wherein the hydrogel member is formed of an agarose gel.

4. The nucleic acid extracting apparatus of claim 3, wherein the agarose gel includes 1% to 2% agarose.

5. The nucleic acid extracting apparatus of claim 3, wherein the agarose gel includes 0.5% to 5% agarose.

6. The nucleic acid extracting apparatus of claim 1, wherein the hydrogel member is adhered to an inner surface of the tube.

* * * * *